(12) United States Patent
Tomaschko et al.

(10) Patent No.: US 7,695,465 B2
(45) Date of Patent: Apr. 13, 2010

(54) CHRONIC TOTAL OCCLUSION DEVICE WITH VARIABLE STIFFNESS SHAFT

(75) Inventors: Daniel K. Tomaschko, Savage, MN (US); Angela Kornkven Volk, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1831 days.

(21) Appl. No.: 10/704,422

(22) Filed: Nov. 7, 2003

(65) Prior Publication Data

US 2004/0073163 A1 Apr. 15, 2004

Related U.S. Application Data

(63) Continuation of application No. 09/918,245, filed on Jul. 30, 2001, now abandoned.

(51) Int. Cl.
*A61M 25/00* (2006.01)
(52) U.S. Cl. .................................. 604/525; 604/524
(58) Field of Classification Search ............ 604/103, 604/528, 103.03, 524, 525
See application file for complete search history.

(56) References Cited

U.S. PATENT DOCUMENTS

| | | | | |
|---|---|---|---|---|
| 3,472,230 A | 10/1969 | Fogarty | ................. | 128/328 |
| 3,592,186 A | 7/1971 | Oster | ................. | 128/2 R |
| 3,683,904 A | 8/1972 | Forster | ................. | 128/127 |
| 3,889,657 A | 6/1975 | Baumgarten | ................. | 128/2 |
| 3,952,747 A | 4/1976 | Kimmell, Jr. | ................. | 128/303 R |
| 3,996,938 A | 12/1976 | Clark, III | ................. | 128/348 |
| 4,046,150 A | 9/1977 | Schwartz et al. | ................. | 128/328 |
| 4,425,908 A | 1/1984 | Simon | ................. | 128/1 |
| 4,447,227 A | 5/1984 | Kotsanis | ................. | 604/95 |
| 4,580,568 A | 4/1986 | Gianturco | ................. | 128/345 |
| 4,590,938 A | 5/1986 | Segura et al. | ................. | 128/328 |
| 4,619,246 A | 10/1986 | Molgaard-Nielsen et al. | .. | 128/1 |
| 4,631,052 A | 12/1986 | Kensey | ................. | 604/22 |
| 4,643,184 A | 2/1987 | Mobin-Uddin | ................. | 128/303 |
| 4,650,466 A | 3/1987 | Luther | ................. | 604/95 |
| 4,662,885 A | 5/1987 | DiPisa, Jr. | ................. | 623/12 |
| 4,705,517 A | 11/1987 | DiPisa, Jr. | ................. | 623/12 |
| 4,706,671 A | 11/1987 | Weinrib | ................. | 128/348.1 |
| 4,723,549 A | 2/1988 | Wholey et al. | ................. | 128/344 |

(Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Nicholas D Lucchesi
*Assistant Examiner*—Victoria P Campbell
(74) *Attorney, Agent, or Firm*—Crompton, Seager & Tufte LLC

(57) ABSTRACT

The present invention relates generally to a device for adding stiffening support to a guidewire so as to enable the guidewire or device to pass through a chronic total occlusion. A method for passing a guidewire through a chronic total occlusion is also disclosed.

11 Claims, 4 Drawing Sheets

U.S. PATENT DOCUMENTS

| | | | |
|---|---|---|---|
| 4,728,319 A | 3/1988 | Masch | 604/22 |
| 4,733,665 A | 3/1988 | Palmaz | 128/343 |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | 128/344 |
| 4,794,931 A | 1/1989 | Yock | 128/660.03 |
| 4,800,882 A | 1/1989 | Gianturco | 128/343 |
| 4,807,626 A | 2/1989 | McGirr | 128/328 |
| 4,842,579 A | 6/1989 | Shiber | 604/22 |
| 4,857,045 A | 8/1989 | Rydell | 604/22 |
| 4,857,046 A | 8/1989 | Stevens et al. | 604/22 |
| 4,867,157 A | 9/1989 | McGurk-Burleson et al. | 128/305 |
| 4,873,978 A | 10/1989 | Ginsburg | 128/345 |
| 4,898,575 A | 2/1990 | Fischell et al. | 604/22 |
| 4,907,336 A | 3/1990 | Gianturco | 29/515 |
| 4,921,478 A | 5/1990 | Solano et al. | 604/53 |
| 4,921,484 A | 5/1990 | Hillstead | 604/104 |
| 4,926,858 A | 5/1990 | Giffort, III et al. | 606/159 |
| 4,950,277 A | 8/1990 | Farr | 606/159 |
| 4,955,895 A | 9/1990 | Sugiyama et al. | 606/194 |
| 4,957,482 A | 9/1990 | Shiber | 604/22 |
| 4,969,891 A | 11/1990 | Gewertz | 606/200 |
| 4,979,951 A | 12/1990 | Simpson | 606/159 |
| 4,986,807 A | 1/1991 | Farr | 604/22 |
| 4,998,539 A | 3/1991 | Delsanti | 128/898 |
| 5,002,560 A | 3/1991 | Machold et al. | 606/198 |
| RE33,569 E | 4/1991 | Gifford, III et al. | 606/159 |
| 5,007,896 A | 4/1991 | Shiber | 604/22 |
| 5,007,917 A | 4/1991 | Evans | 606/170 |
| 5,011,488 A | 4/1991 | Ginsburg | 606/159 |
| 5,019,088 A | 5/1991 | Farr | 606/159 |
| 5,041,126 A | 8/1991 | Gianturco | 606/195 |
| 5,053,008 A | 10/1991 | Bajaj | 604/104 |
| 5,053,044 A | 10/1991 | Mueller et al. | 606/159 |
| 5,071,407 A | 12/1991 | Termin et al. | 604/104 |
| 5,071,425 A | 12/1991 | Gifford, III et al. | 606/159 |
| 5,085,662 A | 2/1992 | Willard | 606/159 |
| 5,087,265 A | 2/1992 | Summers | 606/159 |
| 5,100,423 A | 3/1992 | Fearnot | 606/15 |
| 5,100,424 A | 3/1992 | Jang et al. | 606/159 |
| 5,100,425 A | 3/1992 | Fischell et al. | 606/159 |
| 5,102,415 A | 4/1992 | Guenther et al. | 606/159 |
| 5,104,399 A | 4/1992 | Lazarus | 623/1 |
| 5,106,376 A | 4/1992 | Mononen et al. | 604/164.11 |
| 5,108,419 A | 4/1992 | Reger et al. | 606/200 |
| 5,116,305 A * | 5/1992 | Milder et al. | 600/18 |
| 5,133,733 A | 7/1992 | Rasmussen et al. | 606/200 |
| 5,135,531 A | 8/1992 | Shiber | 606/159 |
| 5,152,771 A | 10/1992 | Sabbaghian et al. | 606/159 |
| 5,152,777 A | 10/1992 | Goldberg et al. | 606/200 |
| 5,160,342 A | 11/1992 | Reger et al. | 606/200 |
| 5,171,233 A | 12/1992 | Amplatz et al. | 604/281 |
| 5,190,546 A | 3/1993 | Jervis | 606/78 |
| 5,195,955 A | 3/1993 | Don Michael | 604/22 |
| 5,224,953 A | 7/1993 | Morgentaler | 606/192 |
| 5,231,989 A | 8/1993 | Middleman et al. | |
| 5,306,286 A | 4/1994 | Stack et al. | 606/198 |
| 5,314,444 A | 5/1994 | Gianturco | 606/195 |
| 5,314,472 A | 5/1994 | Fontaine | 623/12 |
| 5,318,576 A | 6/1994 | Plassche, Jr. et al. | 606/159 |
| 5,329,942 A | 7/1994 | Gunther et al. | 128/898 |
| 5,330,484 A | 7/1994 | Gunther et al. | 606/128 |
| 5,330,500 A | 7/1994 | Song | 606/198 |
| 5,350,398 A | 9/1994 | Pavcnik et al. | 606/200 |
| 5,354,310 A | 10/1994 | Garnic et al. | 606/198 |
| 5,356,423 A | 10/1994 | Tihon et al. | 606/194 |
| 5,366,464 A | 11/1994 | Belknap | 606/159 |
| 5,366,473 A | 11/1994 | Winston et al. | 606/198 |
| 5,370,657 A | 12/1994 | Irie | 606/200 |
| 5,370,683 A | 12/1994 | Fontaine | 623/1 |
| 5,376,100 A | 12/1994 | Lefebvre | 606/180 |
| 5,383,887 A | 1/1995 | Nadal | 606/200 |
| 5,383,892 A | 1/1995 | Cardon et al. | 606/198 |
| 5,383,926 A | 1/1995 | Lock et al. | 623/1 |
| 5,387,235 A | 2/1995 | Chuter | 623/1 |
| 5,395,349 A | 3/1995 | Quiachon et al. | 604/248 |
| 5,397,345 A | 3/1995 | Lazerus | 623/1 |
| 5,405,377 A | 4/1995 | Cragg | 623/1 |
| 5,409,454 A | 4/1995 | Fischell et al. | 604/22 |
| 5,415,630 A | 5/1995 | Gory et al. | 604/53 |
| 5,419,774 A | 5/1995 | Willard et al. | 604/22 |
| 5,421,832 A | 6/1995 | Lefebvre | 604/53 |
| 5,423,742 A | 6/1995 | Theron | 604/28 |
| 5,423,885 A | 6/1995 | Williams | 623/1 |
| 5,425,765 A | 6/1995 | Tiefenbrun et al. | 623/12 |
| 5,443,498 A | 8/1995 | Fontaine | 623/1 |
| 5,449,372 A | 9/1995 | Schmaltz et al. | 606/198 |
| 4,842,579 A | 10/1995 | Shiber | 604/22 |
| 5,456,667 A | 10/1995 | Ham et al. | 604/107 |
| 5,462,529 A | 10/1995 | Simpson et al. | 604/101 |
| 5,476,104 A | 12/1995 | Sheahon | 128/757 |
| 5,484,418 A | 1/1996 | Quiachon et al. | 604/167 |
| 5,499,973 A | 3/1996 | Saab | 604/96.01 |
| 5,507,767 A | 4/1996 | Maeda et al. | 606/198 |
| 5,512,044 A | 4/1996 | Duer | 604/22 |
| 5,527,354 A | 6/1996 | Fontaine et al. | 623/1 |
| 5,536,242 A | 7/1996 | Willard et al. | 604/30 |
| 5,540,707 A | 7/1996 | Ressemann et al. | 606/159 |
| 5,549,626 A | 8/1996 | Miller et al. | 606/200 |
| 5,562,724 A | 10/1996 | Vorwerk et al. | 623/1 |
| 5,569,274 A | 10/1996 | Rapacki et al. | 606/158 |
| 5,569,275 A | 10/1996 | Kotula et al. | 606/159 |
| 5,634,897 A | 6/1997 | Dance et al. | 604/35 |
| 5,658,296 A | 8/1997 | Bates et al. | 606/127 |
| 5,662,671 A | 9/1997 | Barbut et al. | 606/170 |
| 5,669,933 A | 9/1997 | Simon et al. | 600/200 |
| 5,695,519 A | 12/1997 | Summers et al. | 606/200 |
| 5,709,704 A | 1/1998 | Nott et al. | 606/200 |
| 5,720,764 A | 2/1998 | Naderlinger | 606/200 |
| 5,728,066 A | 3/1998 | Daneshvar | 604/96 |
| 5,730,734 A | 3/1998 | Adams et al. | 604/533 |
| 5,746,758 A | 5/1998 | Nordgren et al. | 606/159 |
| 5,749,848 A | 5/1998 | Jang et al. | 604/53 |
| 5,769,816 A | 6/1998 | Barbut et al. | 604/96 |
| 5,779,716 A | 7/1998 | Cano et al. | 606/114 |
| 5,792,300 A | 8/1998 | Inderbitzen et al. | 156/244.13 |
| 5,795,322 A | 8/1998 | Boudewijn | 604/22 |
| 5,797,952 A | 8/1998 | Klein | 606/198 |
| 5,800,457 A | 9/1998 | Gelbfish | 606/200 |
| 5,800,525 A | 9/1998 | Bachinski et al. | 623/1 |
| 5,810,874 A | 9/1998 | Lefebvre | 606/200 |
| 5,814,064 A | 9/1998 | Daniel et al. | 606/200 |
| 5,817,102 A | 10/1998 | Johnson et al. | 606/108 |
| 5,827,324 A | 10/1998 | Cassell et al. | 606/200 |
| 5,833,604 A | 11/1998 | Houser et al. | |
| 5,833,644 A | 11/1998 | Zadno-Azizi et al. | 604/52 |
| 5,833,650 A | 11/1998 | Imran | 604/53 |
| 5,846,260 A | 12/1998 | Maahs | 606/200 |
| 5,848,964 A | 12/1998 | Samuels | 600/200 |
| 5,876,367 A | 3/1999 | Kaganov et al. | 604/8 |
| 5,891,112 A | 4/1999 | Samson | |
| 5,893,867 A | 4/1999 | Bagaoisan et al. | 606/198 |
| 5,895,399 A | 4/1999 | Barbut et al. | 606/159 |
| 5,902,263 A | 5/1999 | Patterson et al. | 604/22 |
| 5,906,618 A | 5/1999 | Larson, III | 606/108 |
| 5,908,395 A | 6/1999 | Stalker et al. | 600/585 |
| 5,908,435 A | 6/1999 | Samuels | 606/200 |
| 5,910,154 A | 6/1999 | Tsugita et al. | 606/200 |
| 5,911,734 A | 6/1999 | Tsugita et al. | 606/200 |
| 5,916,193 A | 6/1999 | Stevens et al. | 604/53 |
| 5,925,016 A | 7/1999 | Chornenky et al. | 604/96 |
| 5,925,060 A | 7/1999 | Forber | 606/191 |
| 5,925,062 A | 7/1999 | Purdy | 606/200 |

| | | | | | | |
|---|---|---|---|---|---|---|
| 5,925,063 A | 7/1999 | Khosravi ............... 606/200 | EP | 0 771 549 A2 | 5/1997 | |
| 5,928,203 A | 7/1999 | Davey et al. ............ 604/247 | EP | 0 784 988 A1 | 7/1997 | |
| 5,928,218 A | 7/1999 | Gelbfish ............... 604/540 | EP | 0 852 132 A1 | 7/1998 | |
| 5,934,284 A | 8/1999 | Plaia et al. ............ 128/898 | EP | 0 934 729 | 8/1999 | |
| 5,935,139 A | 8/1999 | Bates ............... 606/159 | FR | 2 580 504 | 10/1986 | |
| 5,938,645 A | 8/1999 | Gordon ............... 604/264 | FR | 2 643 250 A1 | 8/1990 | |
| 5,941,869 A | 8/1999 | Patterson et al. ......... 604/508 | FR | 2 666 980 | 3/1992 | |
| 5,941,896 A | 8/1999 | Kerr ............... 606/200 | FR | 2 768 326 A1 | 3/1999 | |
| 5,947,995 A | 9/1999 | Samuels ............... 606/200 | GB | 2 020 557 B | 1/1983 | |
| 5,951,585 A | 9/1999 | Cathcart et al. ......... 606/198 | JP | 8-187294 A | 7/1996 | |
| 5,954,745 A | 9/1999 | Gertler et al. ......... 606/200 | SU | 764684 | 9/1980 | |
| 5,976,172 A | 11/1999 | Homsma et al. ......... 606/200 | WO | WO 92/03097 | 3/1992 | |
| 5,989,210 A | 11/1999 | Morris et al. ............ 604/22 | WO | WO 94/14389 | 7/1994 | |
| 5,989,271 A | 11/1999 | Bonnette et al. ......... 606/159 | WO | WO 94/24946 | 11/1994 | |
| 5,989,281 A | 11/1999 | Barbut et al. ............ 606/200 | WO | WO 96/01591 | 1/1996 | |
| 5,993,469 A | 11/1999 | McKenzie et al. ......... 606/159 | WO | WO 96/10375 | 4/1996 | |
| 5,997,557 A | 12/1999 | Barbut et al. ............ 606/159 | WO | WO 96/19941 | 7/1996 | |
| 6,001,118 A | 12/1999 | Daniel et al. ............ 606/200 | WO | WO 96/23441 | 8/1996 | |
| 6,007,557 A | 12/1999 | Ambrisco et al. ......... 606/200 | WO | WO 96/33677 | 10/1996 | |
| 6,010,522 A | 1/2000 | Barbut et al. ............ 606/200 | WO | WO 97/17100 | 5/1997 | |
| 6,013,085 A | 1/2000 | Howard ............... 606/108 | WO | WO 97/27808 | 8/1997 | |
| 6,027,520 A | 2/2000 | Tsugita et al. ............ 606/200 | WO | WO 97/42879 | 11/1997 | |
| 6,051,014 A | 4/2000 | Jang ............... 606/200 | WO | WO 98/02084 | 1/1998 | |
| 6,053,932 A | 4/2000 | Daniel et al. ............ 606/200 | WO | WO 98/02112 | 1/1998 | |
| 6,059,814 A | 5/2000 | Ladd ............... 606/200 | WO | WO 98/23322 | 6/1998 | |
| 6,068,645 A | 5/2000 | Tu ............... 606/200 | WO | WO 98/33443 | 8/1998 | |
| 6,086,605 A | 7/2000 | Barbut et al. ............ 606/200 | WO | WO 98/34673 | 8/1998 | |
| 6,129,739 A | 10/2000 | Khosravi ............... 606/200 | WO | WO 98/36786 | 8/1998 | |
| 6,142,987 A | 11/2000 | Tsugita ............... 604/500 | WO | WO 98/38920 | 9/1998 | |
| 6,152,946 A | 11/2000 | Broome et al. ............ 606/200 | WO | WO 98/38929 | 9/1998 | |
| 6,165,200 A | 12/2000 | Tsugita et al. ............ 606/200 | WO | WO 98/39046 | 9/1998 | |
| 6,168,579 B1 | 1/2001 | Tsugita ............... 604/96.01 | WO | WO 98/39053 | 9/1998 | |
| 6,171,327 B1 | 1/2001 | Daniel et al. ............ 606/200 | WO | WO 98/46297 | 10/1998 | |
| 6,179,851 B1 | 1/2001 | Barbut et al. ............ 606/159 | WO | WO 98/47447 | 10/1998 | |
| 6,179,859 B1 | 1/2001 | Bates et al. ............ 606/200 | WO | WO 98/49952 | 11/1998 | |
| 6,179,861 B1 | 1/2001 | Khosravi et al. ......... 606/200 | WO | WO 98/50103 | 11/1998 | |
| 6,203,561 B1 | 3/2001 | Ramee et al. ............ 606/200 | WO | WO 98/51237 | 11/1998 | |
| 6,214,026 B1 | 4/2001 | Lepak et al. ............ 606/200 | WO | WO 98/55175 | 12/1998 | |
| 6,368,338 B1 | 4/2002 | Konya et al. | WO | WO 99/09895 | 3/1999 | |
| 6,398,798 B2 | 6/2002 | Selmon et al. | WO | WO 99/22673 | 5/1999 | |
| 6,428,552 B1 | 8/2002 | Sparks | WO | WO 99/23976 | 5/1999 | |
| 6,500,166 B1 | 12/2002 | Zadno Azizi et al. | WO | WO 99/25252 | 5/1999 | |
| 6,506,178 B1 | 1/2003 | Schubart et al. | WO | WO 99/30766 | 6/1999 | |
| 6,508,825 B1 | 1/2003 | Selmon et al. | WO | WO 99/40964 | 8/1999 | |
| 6,511,458 B2 | 1/2003 | Milo et al. | WO | WO 99/42059 | 8/1999 | |
| 6,514,217 B1 | 2/2003 | Selmon et al. | WO | WO 99/44510 | 9/1999 | |
| 6,533,753 B1 | 3/2003 | Haarstad et al. | WO | WO 99/44542 | 9/1999 | |
| 6,544,276 B1 | 4/2003 | Azizi | WO | WO 99/55236 | 11/1999 | |
| 6,579,302 B2 | 6/2003 | Duerig et al. | WO | WO 99/58068 | 11/1999 | |
| 6,605,062 B1 | 8/2003 | Hurley et al. | WO | WO 00/07655 | 2/2000 | |
| 2002/0077606 A1* | 6/2002 | Trotta ............... 604/264 | WO | WO 00/09054 | 2/2000 | |
| 2002/0091372 A1* | 7/2002 | Cragg et al. ............ 604/528 | WO | WO 00/16705 | 3/2000 | |
| 2002/0161353 A1* | 10/2002 | Kortelling ............... 604/528 | WO | WO 00/49970 | 8/2000 | |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 517 075 A1 | 12/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . .," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . .," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . .," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

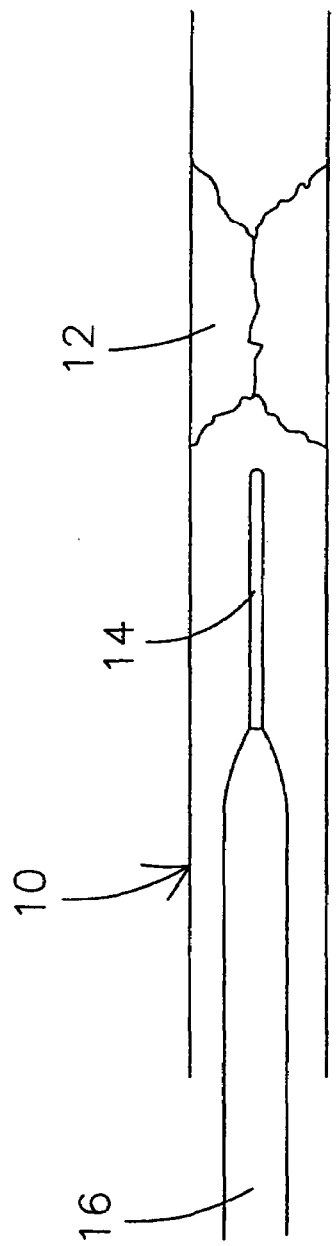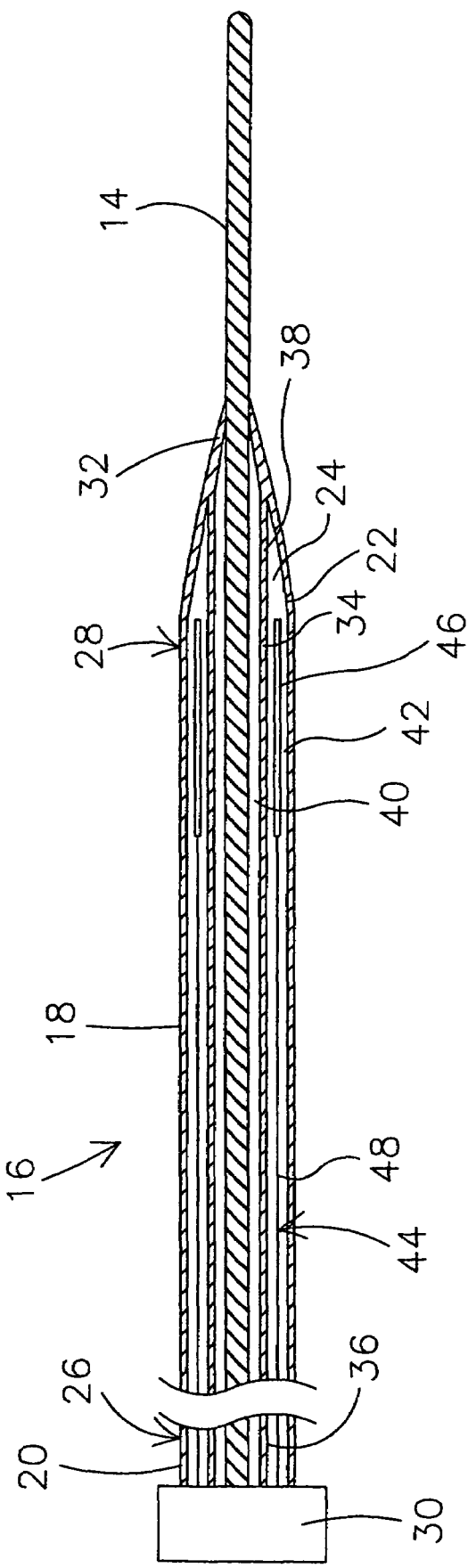

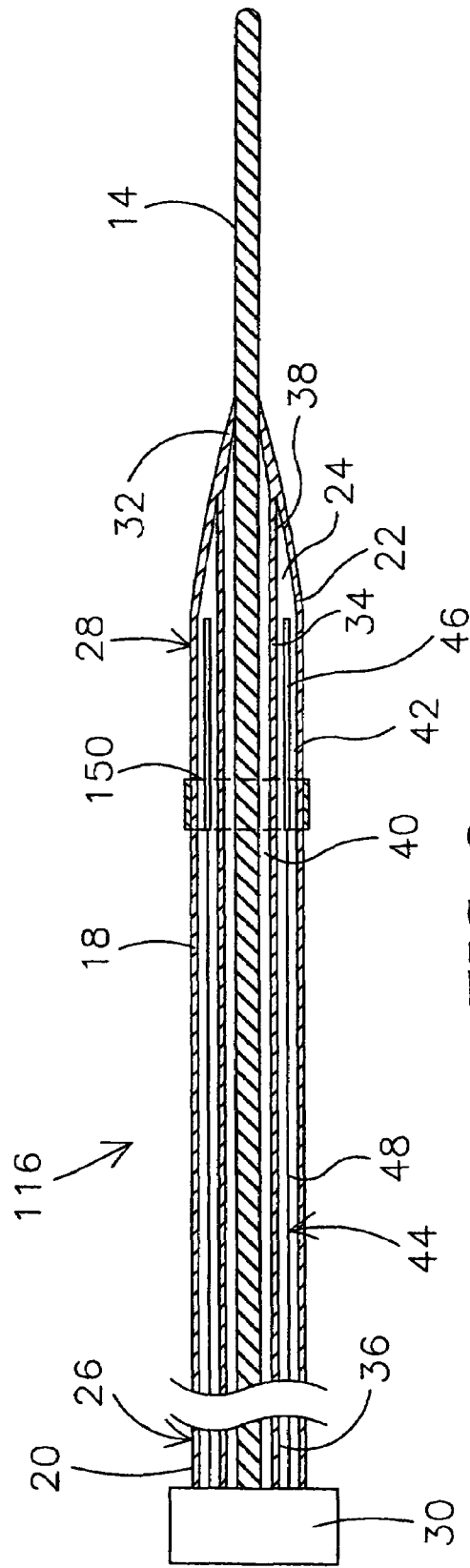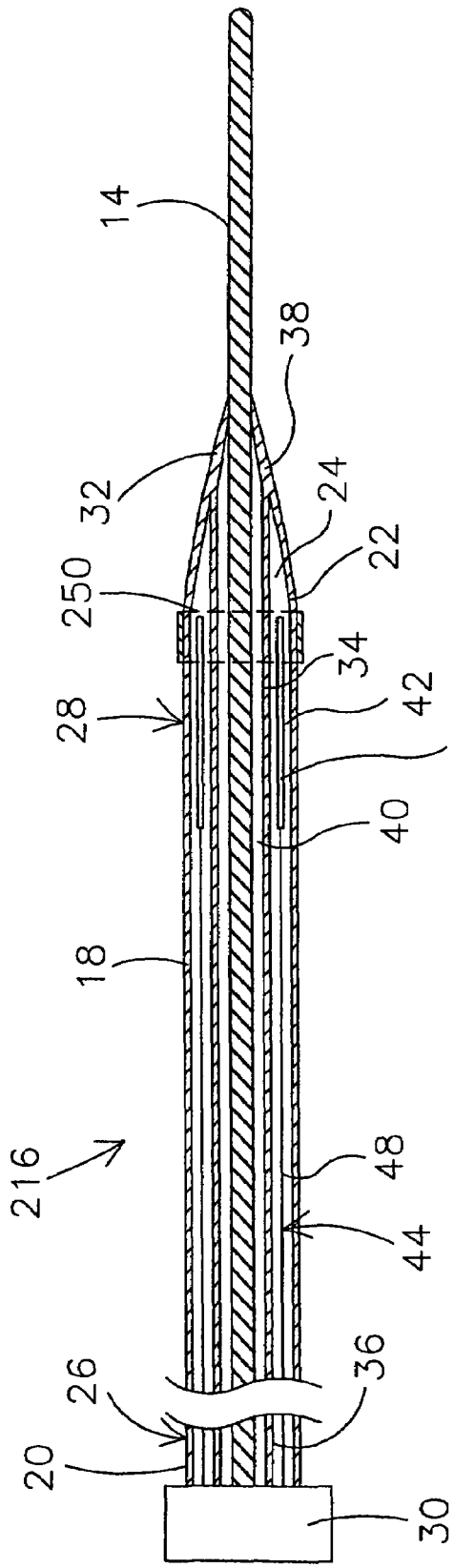

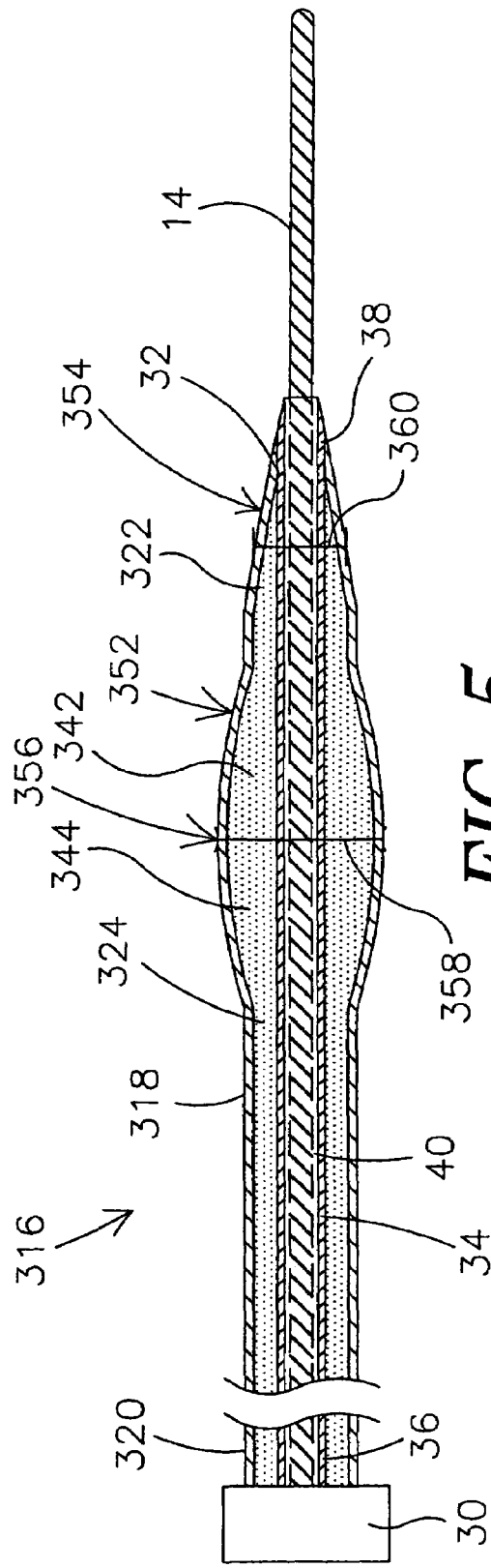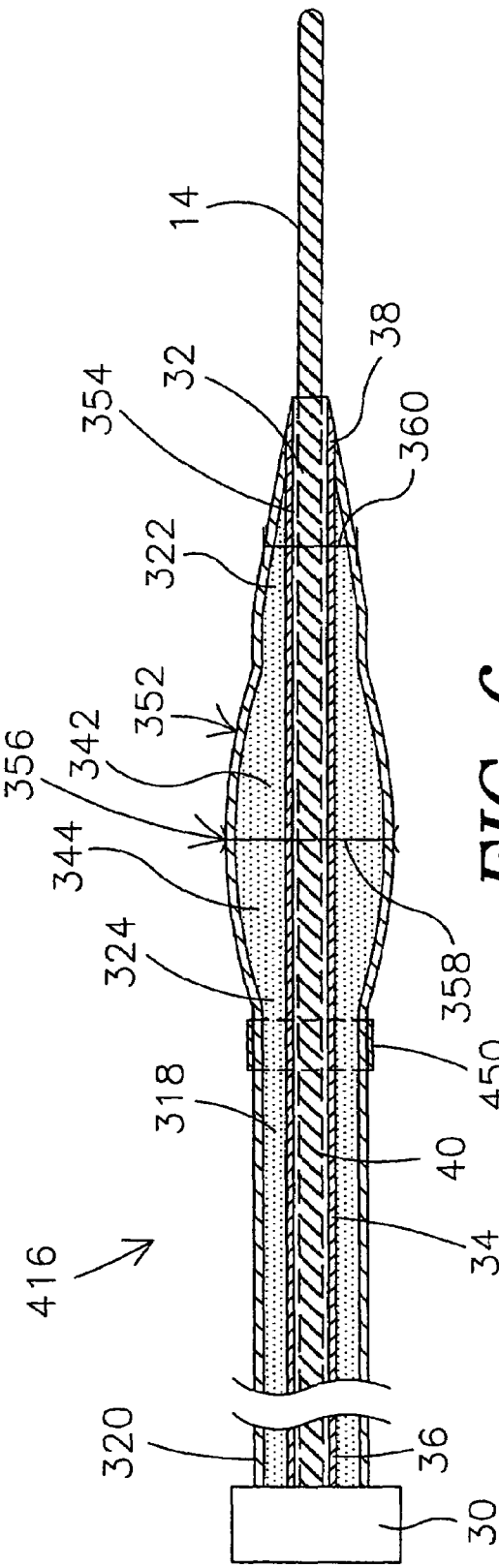

CHRONIC TOTAL OCCLUSION DEVICE WITH VARIABLE STIFFNESS SHAFT

This is a continuation of U.S. application Ser. No. 09/918,245 filed on Jul. 30, 2001 now abandoned.

FIELD OF THE INVENTION

The present invention relates to devices for performing intravascular procedures. More particularly, the present invention relates to devices for adding support to a guidewire so that the guidewire may be passed through a chronic total occlusion.

BACKGROUND OF THE INVENTION

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

Intravascular catheters are commonly used in conjunction with a guidewire. A guidewire may be advanced through the patient's vasculature until it has reached a target location. Once in place, a catheter may be threaded onto the guidewire and urged distally until the distal end of the catheter reaches a target location.

When in use, the guidewire enters the patient's vasculature at a convenient location and then is urged to a target region. The path taken by a catheter through the vascular system is often tortuous, requiring the guidewire to change direction frequently. In order for the guidewire to conform to a patient's tortuous vascular system, it is desirable that it be very flexible, particularly near the distal end.

The guidewire will often confront a stenosis when passing through the vasculature. In addition, the stenosis may completely block the vessel as is the case with a chronic total occlusion. The success of the procedure often depends on the ability to insert the guidewire through the chronic total occlusion.

SUMMARY OF THE INVENTION

The present invention pertains to a chronic total occlusion device that may add support to a guidewire so that the guidewire may pass through a chronic total occlusion. The chronic total occlusion device may comprise an outer tubular member having a proximal end, a distal end, and a lumen extending therethrough. The proximal end may be connectable to a manifold and the distal end may include a distal tip.

An inner tubular member may be disposed within the lumen. The inner tubular member may comprise a proximal end, a distal end, and an inner lumen extending therethrough. The inner lumen may be adapted so that a guidewire may be disposed therein.

An annular space may be formed between the outer tubular member and the inner tubular member. A stiffening member may be disposed within the annular space. The stiffening member may comprise a distal head and a proximal tail. The proximal tail may be more stiff than the distal head. In an exemplary embodiment, the stiffening member is movable relative to the outer tubular member. The manifold may comprise a means for controlling the stiffening member.

The outer tubular member may further comprise an expandable region. The expandable region may further comprise a first region and a second region. The first region may include a first outside diameter. The second region may include a second outside diameter that, when expanded, is generally smaller than the outside diameter of a typical angioplasty balloon. According to this embodiment, the stiffening member may comprise inflation medium, liquid, or gas. Additionally, the manifold may include an inflation medium pump capable of pumping the inflation medium into the expandable region so that the chronic total occlusion device may add stiffness to the guidewire, dilate the vessel, anchor the device, or center the guidewire.

The chronic total occlusion may further comprise a marker band. The marker band may be disposed proximal of the distal tip. Alternatively, the marker band may be disposed at the distal tip.

BRIEF DESCRIPTION OF THE DRAWINGS

FIG. 1 is a side view of a chronic total occlusion device according to a preferred embodiment of the invention disposed within a vessel;

FIG. 2 is a cross sectional view of a chronic total occlusion device according to a preferred embodiment of the invention;

FIG. 3 is a cross sectional view of an alternate embodiment of the chronic total occlusion device shown in FIG. 2;

FIG. 4 is a cross sectional view of a second alternate embodiment of the chronic total occlusion device shown in FIG. 2;

FIG. 5 is a cross sectional view of an alternate chronic total occlusion device according to a preferred embodiment of the invention;

FIG. 6 is a cross sectional view of an alternate embodiment of the chronic total occlusion device shown in FIG. 5.

DETAILED DESCRIPTION OF THE PREFERRED EMBODIMENTS

Figure 7:
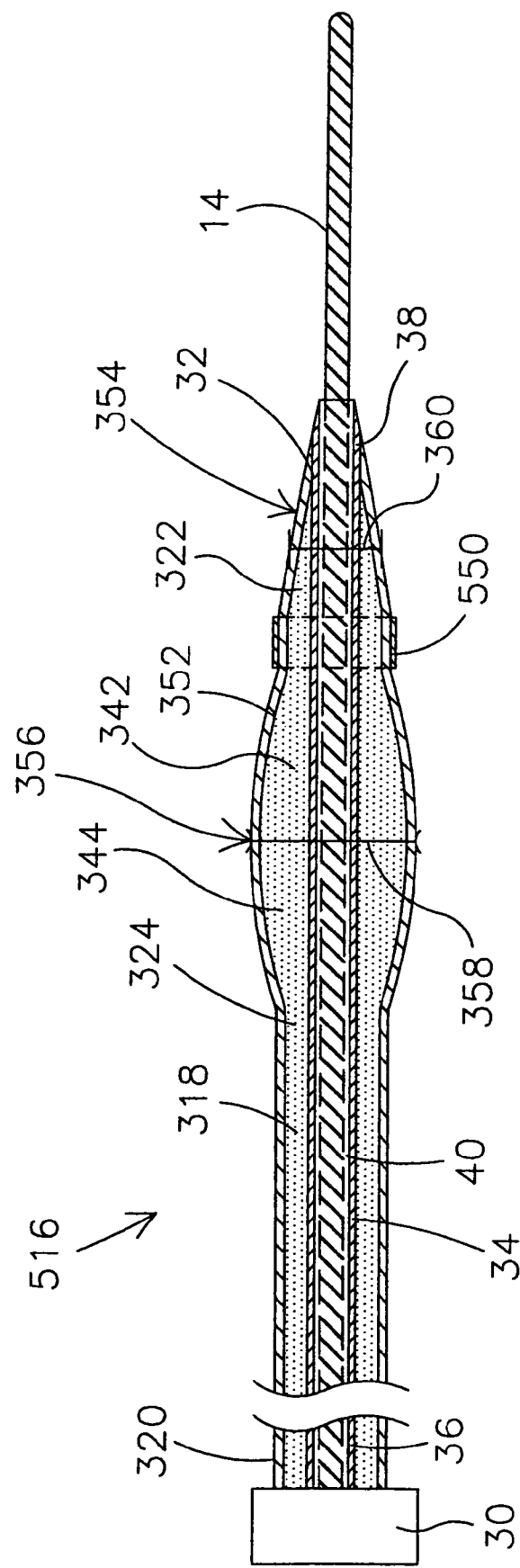
FIG. 7 is a cross sectional view of a second alternate embodiment of the chronic total occlusion device shown in FIG. 5.

The following description should be read with reference to the drawings wherein like reference numerals indicate like elements throughout the several views. The detailed description and drawings illustrate example embodiments.

FIG. 1 is a side view of a chronic total occlusion device. Along the length of a blood vessel 10, a chronic total occlusion 12 may be present. Chronic total occlusion 12 is understood to be a partial or complete blockage of blood vessel 10 and may comprise a calcified lesion, an atherosclerotic lesion, a stenosis, etc. Chronic total occlusion 12 may occlude blood vessel 10 so as to substantially prevent the passage of a guidewire 14 therethrough. In order for guidewire 14 to pass chronic total occlusion 12, it may need added stiffening support. Stiffening support for guidewire 14 may include a chronic total occlusion device 16.

Chronic total occlusion device 16 may be used to stiffen guidewire 14 in conjunction with a number of medical procedures. Chronic total occlusion device 16 may be used with a device or method that utilizes an intravascular guidewire. For example, chronic total occlusion device 16 may be used during percutaneous transluminal angioplasty (PTA), percutaneous transluminal coronary angioplasty (PTCA), atherectomy, or other vascular procedures.

FIG. 2 is a detailed view of chronic total occlusion device 16. Chronic total occlusion device 16 may comprise an outer tubular member 18 having a proximal end 20, a distal end 22, and a lumen 24 extending therethrough. The length of chronic total occlusion device 16 may be about equal to a typical angioplasty catheter. For example, chronic total occlusion device may be about 50-200 cm long.

Outer tubular member 18 may be comprised of materials including, but not limited to, metals, stainless steel, nickel alloys, nickel-titanium alloys, nitinol, thermoplastics, high performance engineering resins, fluorinated ethylene propylene (FEP), polymer, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, or perfluoro (propyl vinyl ether) (PFA), and combinations thereof.

Outer tubular member 18 may be subdivided into a proximal segment 26 and a distal segment 28. According to this embodiment, proximal segment 26 may be comprised of CRISTAMID® 11200, which is a semi-aromatic co-polyamide polymer commercially available from Atochem and is the subject of U.S. Pat. No. 4,898,896, hereby incorporated by reference. Distal segment 28 may be comprised of polyether block amide (PEBA). Polyether block amide is commercially available from Atochem Polymers of Birdsboro, Pa., under the trade name PEBAX®. Distal segment 28 may have increased flexibility relative to proximal segment 26.

Proximal end 20 may be connectable to a manifold 30. Proximal end 20 may be bonded to manifold 30 with an adhesive. Alternatively, proximal end 20 may further comprise a luer adapter that is connectable to manifold 30. Distal end 22 may include a distal tip 32 that may be tapered. In an exemplary embodiment, distal tip 32 may be comprised of Grilamid® (ELY 2694, a nylon 12 elastomer), which is commercially available from EMS-Chemie.

An inner tubular member 34 may be disposed within Lumen 24. Inner tubular member 34 may be generally coaxial with outer tubular member 18. Inner tubular member 34 may comprise a proximal end 36, a distal end 38, and an inner lumen 40 extending therethrough. Inner tubular member 34 may comprise an inner layer of high density polyethylene (HDPE, namely MARLEX® HHM 4903, commercially available from Phillips Petroleum), an outer layer of polyether block amide (PEBAX® 7233), and a tie-layer of PLEXAR® 3080 to adhere the layers. PLEXAR® is a known tie layer material that is a modified low density polyethylene, commercially available from Equistar Chemicals, LP. Inner layer 34 may be manufactured by coextrusion of the above materials. Alternatively, inner tubular member 34 may be comprised of materials similar to those disclosed above for outer tubular member 18.

Inner lumen 40 may be adapted so that guidewire 14 may be disposed therein. Inner lumen 40 has an inside diameter appropriate to accommodate multiple embodiments of guidewire 14 having differing outside diameters. For example, inner lumen 40 may accommodate guidewire 14 having an outside diameter less than about 0.038-0.008 inches. Alternatively, inner lumen 40 may accommodate guidewire 14 having an outside diameter less than about 0.014 inches. Inner lumeri 40 may further comprise a lubricious liner. The lubricious liner may comprise polytetrafluoroethylene.

Although inner lumen 40 may have an inside diameter of appropriate size for many embodiments of guidewire 14, alteration of the inside diameter of inner lumen 40 may occur while maintaining the generally small profile of chronic total occlusion device 16 and, thus, the ability of outer tubular member 18 to pass through tight stenotic vasculature. According to this embodiment, the outside diameter of outer tubular member 18 may be less than about 0.200-0.500 inches.

An annular space 42 may be formed between outer tubular member 18 and inner tubular member 34. A stiffening member 44 may be disposed within annular space 42. Stiffening member 44 may comprise a number of materials similar to those listed above including metals and polymers. In addition, stiffening member 44 may comprise a wire or stiffening sleeve.

Stiffening member 44 may further include a distal head 46 and a proximal tail 48. Proximal tail 48 may be more stiff than distal head 46. Stiffening member 44 may be movable relative to outer tubular member 18. Actuation of stiffening member 44 can, thus, vary the stiffness of chronic total occlusion device 16 along the length of outer tubular member 18. For example, actuation of stiffening member 44 may comprise moving distal head 46 toward distal end 22. Actuation may result in increased stiffness of chronic total occlusion device 16 near distal end 22. Increased stiffness may enable chronic total occlusion device 16 to provide stiffness support to guidewire 14 so that guidewire 14 may pass through chronic total occlusion 12.

Manifold 30 may further comprise means for controlling stiffening member 44. Means for controlling stiffening member 44 may include an access port to proximal tail 48. According to this embodiment, manifold 30 may comprise an opening that may allow a clinician to grasp and move proximal tail 48 relative to outer tubular member 18. Additional means for controlling stiffening member 44 may include a handle assembly comprising an actuation button, wheel, lever, or slidable object wherein actuation of the means for controlling stiffening member 44 substantially results in movement of stiffening member 44 relative to outer tubular member 18. Moreover, the coupling of proximal tail 48 to manifold 30 may add further support along the length of guidewire 14 during, for example, exchange of catheters over guidewire 14 and for exchange of guidewires.

In use, chronic total occlusion device 16 or alternates thereof may be used in multiple ways to add support to guidewire 14. For example, chronic total occlusion device may be passed over guidewire 14 if chronic total occlusion 12 is encountered while steering guidewire 14 through blood vessel 10. According to this embodiment, guidewire 14 may be steered through blood vessel 10 until encountering chronic total occlusion 12, chronic total occlusion device 16 may be passed over guidewire 14, and chronic total occlusion device 16 (with guidewire 14 disposed in inner lumen 40) may pass chronic total occlusion 12. During the step of encountering or passing chronic total occlusion 12, chronic total occlusion device 12 may pre-dilate blood vessel 10 which may aid further dilation, for example, by an angioplasty catheter or stent. If desired, chronic total occlusion device 14 may be withdrawn from guidewire 14 until a further chronic total occlusion is encountered. Further, an alternative embodiment of chronic total occlusion device 16 comprises a single-operator-exchange catheter including a proximal guidewire port proximate distal end 22. The inclusion of the port may facilitate easier exchange of catheters along guidewire 14.

Alternatively, guidewire 14 may be disposed within inner lumen 40 while chronic total occlusion device 16 is steered through blood vessel 10. According to this embodiment, chronic total occlusion device 16 (with guidewire 14 disposed in inner lumen 40) may be steered through blood vessel 10 so as to more easily pass chronic total occlusion 12 when encountered. Similar to what is stated above, this method may be used in accordance with the single-operator-exchange embodiment disclosed above.

FIG. 3 is a cross sectional view of an alternate embodiment of chronic total occlusion device 16 shown in FIG. 2. Chronic total occlusion 116 is essentially similar to chronic total occlusion device 16 except it further comprises a marker band 150. Marker band 150 may be disposed near distal tip 32.

Marker band 150 may produce a relatively bright image on a fluoroscopy screen during a medical procedure. This relatively bright image may aid the user of chronic total occlusion device 16 in determining the location of distal end 22 of outer tubular member 18. Marker band 50 may comprise a number of radiopaque materials including, but not limited to, gold, platinum, and plastic material loaded with a radiopaque filler. Chronic total occlusion device 16 may further comprise additional marker bands or may comprise a marker band disposed at a different location. For example, chronic total occlusion device 16 may comprise a first marker band (e.g., marker band 150) a fixed distance from distal end 22 of outer tubular member 18. A second marker band may be disposed on outer tubular member 18 proximally a distance that is approximately equal to the distance the first marker band is from distal end 22.

FIG. 4 is a cross sectional view of a second alternate embodiment of chronic total occlusion device 16 shown in FIG. 2. Chronic total occlusion 216 is essentially similar to chronic total occlusion device 16 except it further comprises marker band 250 disposed at distal tip 32. Marker band 250 may comprise a radiopaque additive that may be impregnated within distal tip 32. This method of disposing marker band 250 at distal tip 32 may help prevent or avoid weeping of the radiopaque materials into the body of a patient.

FIG. 5 is a detailed view of an alternate chronic total occlusion device. Chronic total occlusion device 316 is essentially similar to chronic total occlusion device 16 except that outer tubular member 318 further comprises an expandable region 352 in addition to proximal end 320, distal end 322, and lumen 324 extending therethrough. Expandable region 352 may comprise a balloon. Expandable region 352 may be formed by alternatively processing outer tubular member 318. For example, alternative processing of outer tubular member 318 may include blow molding, changing dimensions, chemically changing, forming of differing materials including materials capable of self-collapsing after inflation, etc.

Expandable region 352 may further comprise a first region 354 and a second region 356. First region 354 may include a first outside diameter 360. Second region 356 may include a second outside diameter 358 that, when expanded, may be generally smaller than the outside diameter of a typical angioplasty balloon. Moreover, first outside diameter 360 may be generally smaller than second outside diameter 358. Maintaining a generally smaller profile than a typical angioplasty balloon may allow chronic total occlusion device 316 to be steered through stenotic vasculature.

Stiffening member 344 may be disposed within expandable region 352. Stiffening member 344 may comprise inflation medium, liquid, or gas. According to this embodiment, stiffening member 344 can be moved along outer tubular member 318 to expandable region 352.

Annular space 342 may be in fluid communication with expandable region 352. Manifold 30 may further comprise means for controlling stiffening member 344. Means for controlling stiffening member 344 may include an inflation medium pump capable of pumping stiffening member 344 into expandable region 352. For example, manifold 30 may include an inflation medium pump suitable for pumping inflation fluid into expandable region 352.

In use, chronic total occlusion device 316 may be used substantially similar to chronic total occlusion device 16. Actuation of stiffening member 344 may comprise expanding expandable region 352 by passing stiffening member 344 into expandable region when guidewire 14 is disposed within inner tubular member 34. Actuation of stiffening member 344 may provide stiffening support to guidewire 14. Passing stiffening member 344 into expandable region may result in little or no expansion of expandable region 352. According to this embodiment, actuation of stiffening member 344 is understood to stiffen chronic total occlusion device 316 by adding tension to outer tubular member 318. Expandable region 352 may, thus, comprise materials that are substantially resistant to expansion.

FIG. 6 is a detailed view of an alternate embodiment of the chronic total occlusion device shown in FIG. 5. Chronic total occlusion 416 is essentially similar to chronic total occlusion device 316 except it further comprises a marker band 450. Marker band 450 may be disposed near distal tip 32 or may be disposed proximal of distal tip 32.

FIG. 7 is a detailed view of a second alternate embodiment of the chronic total occlusion device shown in FIG. 5. Chronic total occlusion 516 is essentially similar to chronic total occlusion device 316 except it further comprises marker band 550 disposed at distal tip 32. Similar to what is disclosed above, marker band 550 may comprise a radiopaque additive that may be impregnated within distal tip 32.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A chronic total occlusion device, comprising:
an inner tubular member having an inner lumen, the inner lumen sized for having a guidewire disposed therein;
an outer tubular member disposed over the inner tubular member, the outer tubular member having a proximal end region and a distal end region;
wherein an annular lumen is defined between the outer tubular member and the inner tubular member;
wherein the outer tubular member distally tapers so that the annular lumen is smaller adjacent the distal end region of the outer tubular member than adjacent the proximal end region of the outer tubular member; and
a stiffening member having a distal head and a proximal tail, the proximal tail having a stiffness different than that of the distal head, movably disposed within the annular lumen, further comprising means for controlling the stiffening member.

2. The device of claim 1, wherein the chronic total occlusion device has a distal flexibility and wherein the distal flexibility is variable depending on the position of the stiffening member within the annular lumen.

3. The device of claim 1, wherein the stiffening member includes an enlarged distal head and an elongate proximal tail.

4. The device of claim 1, further comprising a second stiffening member.

5. The device of claim 1, further comprising a marker band coupled to the outer tubular member.

6. A variable stiffness chronic total occlusion device for use with an intravascular guidewire, comprising:
- an inner tubular member having a guidewire lumen extending therethrough;
- an outer tubular member disposed over the inner tubular member;
- wherein an annular space is defined between the outer tubular member and the inner tubular member;
- a stiffening member having a distal head and a proximal tail, the proximal tail having a stiffness different than that of the distal head slidably disposed within the annular space; and
- wherein the stiffening member is configured to shift within the annular space between a first position that defines a first distal flexibility for the chronic total occlusion device and a second position that defines a second distal flexibility for the chronic total occlusion device.

7. The device of claim 6, wherein the stiffening member includes an enlarged distal head and an elongate proximal tail.

8. The device of claim 6, further comprising a second stiffening member.

9. The device of claim 6, further comprising means for controlling the stiffening member.

10. The device of claim 6, further comprising a marker band coupled to the outer tubular member.

11. The device of claim 6, wherein the outer tubular member distally tapers so that the annular space is smaller adjacent the distal end region of the outer tubular member than adjacent the proximal end region of the outer tubular member.

* * * * *